US009649183B2

(12) United States Patent
McKinnis et al.

(10) Patent No.: US 9,649,183 B2
(45) Date of Patent: May 16, 2017

(54) APPARATUS AND METHOD FOR THE DELIVERY OF AN INTRAVASCULAR FILTER

(71) Applicant: Muffin Incorporated, West Lafayette, IN (US)

(72) Inventors: Peter S. McKinnis, West Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 0 days.

(21) Appl. No.: 14/086,208

(22) Filed: Nov. 21, 2013

(65) Prior Publication Data

US 2014/0172007 A1    Jun. 19, 2014

Related U.S. Application Data

(60) Provisional application No. 61/739,070, filed on Dec. 19, 2012.

(51) Int. Cl.
     *A61F 2/01*          (2006.01)

(52) U.S. Cl.
     CPC ........... *A61F 2/01* (2013.01); *A61F 2002/011* (2013.01); *A61F 2002/016* (2013.01); *A61F 2230/005* (2013.01); *A61F 2230/0067* (2013.01)

(58) Field of Classification Search
     CPC A61F 2002/011; A61F 2/01; A61F 2002/016; A61F 2002/018; A61F 2230/0067; A61F 2230/0006; A61F 2230/08; A61F 2230/005; A61F 2/013; A61B 17/50; A61B 17/221; A61B 17/32056; A61B 2017/22035; A61B 2017/2212; A61B 2017/2215; A61B 2017/00358; A61B 8/445; A61B 8/4461; A61B 8/0841; A61B 8/4245;
(Continued)

(56) References Cited

U.S. PATENT DOCUMENTS 3,672,367 A    6/1972   Scislowicz
4,525,157 A    6/1985   Vaillancourt
(Continued)

FOREIGN PATENT DOCUMENTS

WO    WO 98/50103 A1    12/1998
WO    WO 2005/102211 A1    11/2005
(Continued)

OTHER PUBLICATIONS

International Search Report and Written Opinion issued in PCT/US2013/071264, dated Mar. 10, 2014.
EP Search Report from EP13864888.6 dated Jun. 9, 2016.

*Primary Examiner* — Robert Lynch
*Assistant Examiner* — Socrates L Boutsikaris
(74) *Attorney, Agent, or Firm* — Woodard Emhardt Moriarty McNett & Henry LLP (57) ABSTRACT

A delivery apparatus for introducing an intravascular filter into a body vessel of a patient includes a sheath defining a lumen, an intravascular filter positioned in the lumen, an ultrasound transducer positioned to the application side of the intravascular filter, a guide wire cannula and a tip located at an application side end of the delivery apparatus.

29 Claims, 7 Drawing Sheets

(58) Field of Classification Search
CPC ... A61B 2090/3925; A61B 1/018; A61B 1/05; A61B 2090/378; A61B 6/12; A61B 90/36
USPC ........................................................ 606/200
See application file for complete search history.

(56) References Cited

U.S. PATENT DOCUMENTS

| | | | |
|---|---|---|---|
| 4,917,097 A * | 4/1990 | Proudian | A61B 8/12 600/463 |
| 5,324,304 A | 6/1994 | Rasmussen | |
| 5,415,630 A | 5/1995 | Gory et al. | |
| 6,080,178 A | 6/2000 | Meglin | |
| 6,120,494 A | 9/2000 | Jonkman | |
| 6,440,077 B1 | 8/2002 | Jung et al. | |
| 6,645,152 B1 | 11/2003 | Jung et al. | |
| 7,591,813 B2 | 9/2009 | Levine et al. | |
| 7,625,390 B2 | 12/2009 | Hendriksen et al. | |
| 7,699,867 B2 | 4/2010 | Hendriksen et al. | |
| 7,717,865 B2 | 5/2010 | Boutillette et al. | |
| 7,803,171 B1 | 9/2010 | Uflacker | |
| 8,043,324 B2 | 10/2011 | Deshpande et al. | |
| 2004/0230220 A1 | 11/2004 | Osborne | |
| 2006/0069405 A1* | 3/2006 | Schaeffer et al. | 606/200 |
| 2006/0106417 A1* | 5/2006 | Tessmer et al. | 606/200 |
| 2008/0103456 A1 | 5/2008 | Johnson et al. | |
| 2008/0119867 A1 | 5/2008 | Delaney | |
| 2009/0118760 A1 | 5/2009 | Clausen et al. | |
| 2009/0326560 A1 | 12/2009 | Lampropoulos et al. | |
| 2011/0237955 A1* | 9/2011 | Dietz et al. | 600/466 |
| 2012/0022578 A1 | 1/2012 | Jantzen et al. | |
| 2012/0041473 A1 | 2/2012 | Nigon | |
| 2012/0172920 A1* | 7/2012 | Fifer et al. | 606/200 |
| 2012/0239130 A1* | 9/2012 | Hartley | A61F 2/95 623/1.12 |

FOREIGN PATENT DOCUMENTS

| | | |
|---|---|---|
| WO | WO 2007/079415 A2 | 7/2007 |
| WO | WO 2012/003369 A2 | 1/2012 |

* cited by examiner

APPARATUS AND METHOD FOR THE DELIVERY OF AN INTRAVASCULAR FILTER

CROSS REFERENCE TO RELATED APPLICATION

This application claims the benefit of U.S. Provisional Application No. 61/739,070 filed Dec. 19, 2012, which is hereby incorporated by reference.

BACKGROUND

Disclosed is an apparatus for use in the delivery of an intravascular filter. Also disclosed is a method of using the disclosed apparatus in the delivery of an intravascular filter.

The intravascular filter is constructed and arranged for use in the circulatory system for capturing emboli. As used herein, the term "emboli" refers to something which travels through the bloodstream and which has a structural configuration and composition such that it could become lodged in a blood vessel and creates some degree of blockage to flow through the blood vessel. Examples of emboli include a detached blood clot or a larger piece of a blood clot, a clump of bacteria, stenosed material and more generically, something which could pose a risk of creating an obstruction. A pulmonary embolism occurs when a blood clot dislodges from the wall of a vein and migrates to the lung where it blocks blood flow in the pulmonary artery. Such clots are more likely in patients immobilized by disease, injury or following surgeries. Since a pulmonary embolism can cause severe patient injury or even death, there is a need for intravascular filters of the type described herein. More specifically, there is a need to have a safe and effective inferior vena cava (IVC) filter.

The design focus of an intravascular filter, such as an IVC filter, is on providing a structure which is capable of trapping these emboli so as to prevent them from reaching the heart and lungs. In order to have a safe and effective treatment, the design and construction of the intravascular filter is important as well as the design and construction of the delivery apparatus. The method of using the delivery apparatus for placement and positioning of the intravascular filter is also important.

The specific focus of the disclosed apparatus and method, as exemplified by the illustrated and described embodiments, is directed to the delivery of an intravascular filter into the inferior vena cava (IVC). The IVC is the large vein in the abdomen that returns blood from the lower body to the heart. As such, the IVC represents a preferred location for an intravascular filter to capture, trap and retain emboli, such as detached blood clots or larger pieces of blood clots which may develop in the veins of the leg or pelvis. Blood clots that develop in the veins of the leg or pelvis, a condition called deep vein thrombosis (DVT), occasionally break up and a larger piece of the clot can travel to the heart and lungs. The flow path to the heart and lungs includes passage through the IVC. This makes the IVC a suitable location for the placement and positioning of a capturing intravascular filter, such as the IVC filter which is disclosed herein.

The prior art includes IVC filters constructed and arranged as permanently installed devices. However, there can be long term risks associated with leaving the IVC filter in place. Therefore, more recently design efforts have been directed to the design and construction of IVC filters for temporary placement and subsequently retrieval and removal. The removal of the IVC filter from the patient may be performed when the risk of a traveling emboli, such as a detached blood clot (or a larger piece of a clot or other emboli) has passed. Once the risk of a traveling emboli reaching the heart and lungs has lessened, removal of the IVC filter can be considered.

As with any device or apparatus which is emplaced, implanted or in some fashion delivered into a patient, the ease of delivery is important. It is also important to be able to ensure the proper placement and positioning of the device. With certain devices, if the initial positioning of the device is not within the acceptable parameters, the device may have to be retrieved and removed and the procedure repeated. Therefore, the manner of guidance for the device, the reliability of the procedure and the repeatability of the procedure are important aspects. It is also important with any such device or apparatus which is to be removed from the patient at some point in time to have a design for that device which enables and facilitates retrieval and removal.

Another aspect of the delivery process is the manner in which it can be performed and the required environment for performing that procedure. The prior art procedure is currently performed under fluoroscopic guidance. A percutaneous delivery set and fluoroscopy suite are required to perform the prior art procedure. Further, transport of the patient to the fluoroscopy suite is required and this can be difficult and time consuming, especially for trauma patients. The procedure according to the present disclosure instead uses an intravascular ultrasound (IVUS) transducer for visual guidance. Importantly, the entire ultrasound procedure is able to be performed, according to the present disclosure, without removing the IVUS transducer until the IVC filter is essentially fully emplaced. The withdrawal of the IVUS transducer from the vein enables the clinician to verify the final positioning and emplacement of the IVC filter. This means that during dilation, sheath placement, filter delivery and placement verification are able to be performed by means of a safer procedure. As a further benefit, the clinician has higher confidence in the procedure because the clinician is able to "see" what is happening based on ultrasound imaging. The described IVUS procedure is able to be performed bedside which reduces cost and improves safety.

SUMMARY

A delivery apparatus for introducing an intravascular filter into a body vessel of a patient includes a sheath defining a lumen, an intravascular filter positioned in the lumen, an ultrasound transducer positioned to the application side of the intravascular filter, a guide wire cannula and a tip located at the application end of the delivery apparatus adjacent an end of the guide wire cannula.

A delivery apparatus for the placement of an IVC filter in the inferior vena cava of a patient, the delivery apparatus including a sheath defining a lumen, an IVC filter positioned in the lumen, an IVUS transducer positioned to the application side of the IVC filter, a guide wire cannula and dilator assembled to the guide wire cannula, the IVUS transducer being positioned between the dilator and the IVC filter.

A method of introducing an intravascular filter into a body vessel of a patient using a delivery apparatus as disclosed herein includes the steps of providing an appropriate delivery apparatus, inserting that delivery apparatus into a body vessel of a patient, positioning the delivery apparatus within an imaging plane of an ultrasound transducer, manipulating the delivery apparatus so as to move a portion of the intravascular filter into the imaging plane of the transducer and withdrawing the delivery apparatus without the intravascular filter which remains in the body vessel.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 1:
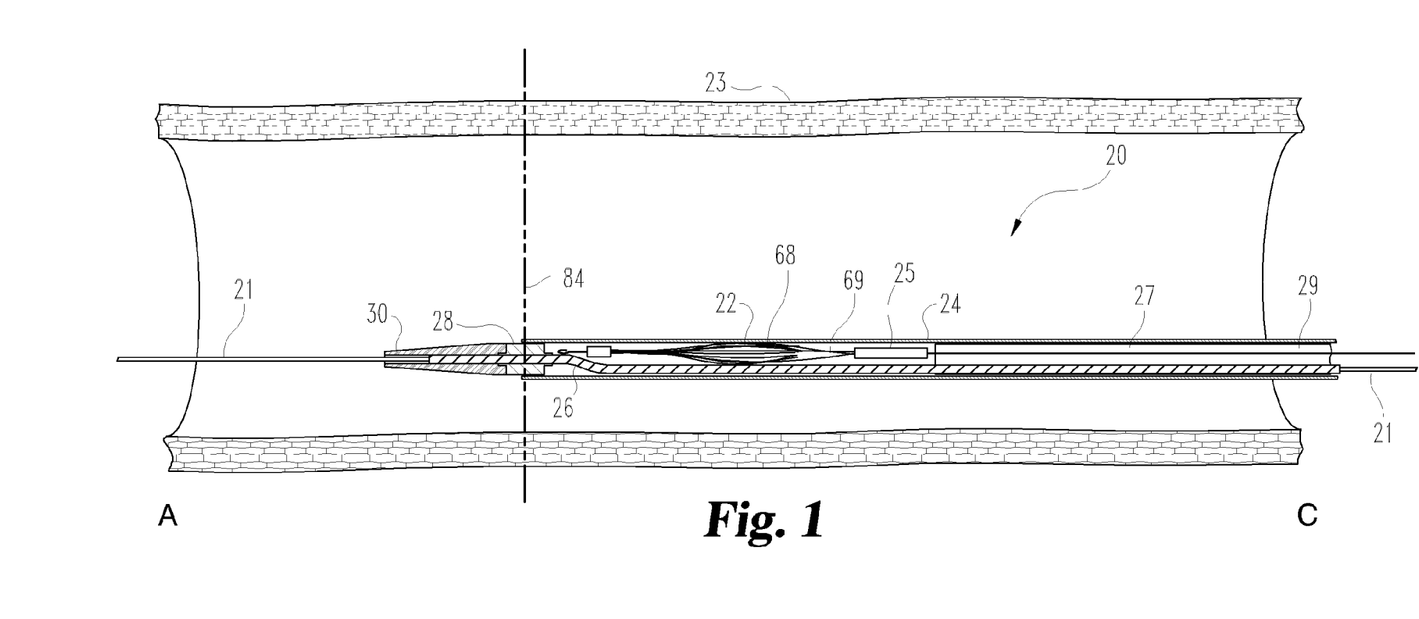
FIG. 1 is a diagrammatic, side elevational view, in partial section, of a delivery apparatus for an intravascular filter according to the present disclosure.

Referring to FIG. 1, there is illustrated a delivery apparatus 20 for an intravascular filter 22. In the exemplary embodiment filter 22 is an IVC filter as defined by its positioning in the inferior vena cava (IVC) 23. The IVC filter 22 is initially packaged within the delivery apparatus 20 and as used herein, the delivery apparatus 20 is defined as including the IVC filter 22 which is being delivered into the IVC 23. However, it is to be understood that since this is a delivery apparatus, the component which is being "delivered" into the patient is the IVC filter 22. Once deployed and properly positioned (i.e. emplaced), the delivery apparatus 20 is removed from the patient without the IVC filter 22. A section of the IVC 23 is illustrated in FIG. 1 for assisting with an understanding of the orientation and the relative positioning of delivery apparatus 20 and for a size perspective. In addition to IVC filter 22, delivery apparatus 20 includes an outer sheath 24, a guide wire cannula 26, an ultrasound transducer 28 and a tip which in the exemplary embodiment is dilator 30. As shown in FIG. 1, the letter A denotes the application side, end or direction referred to herein and the letter C denotes the control side, end or direction as referred to herein.

In terms of orienting the ends of the delivery apparatus 20 and the ends or sides of the component parts and the directions of movement or travel, the conventions of "application side" (A) and "control side" (C) have been adopted and are used herein. As these phrases imply, the application side of either apparatus 20 or of any of the component parts is the side or end which is in the direction or closer to where any treatment, device placement, etc. occurs. Similarly, the control side is the side or end of apparatus 20 or any of the component parts which is in the direction of or closer to where the physician is positioned and denotes where control functions or actions would be performed.

One reason for this adoption is for added clarity since there can be different frames of reference when using "proximal" and "distal". In the medical field "proximal" typically means closer to the heart, but this can change based on the point of entry of a device, such as a catheter, into a patient. Logically, in the medical field, "distal" typically means further from the heart. In other fields, "proximal" typically means closer to the operator or user and "distal" typically means further from the operator or user. By adopting the conventions of "application side" and "control side", any proximal-distal ambiguity should be eliminated.

Further components which are a part of delivery apparatus 20 include filter delivery device 25, control wire 27 and catheter 29. In the exemplary embodiment, the catheter 29 is a three (3) lumen catheter. One lumen receives the guide wire cannula 26 and another lumen is used for the wiring which connects to the ultrasound transducer 28. The filter 22 and the filter delivery device 25 are not inside a dedicated lumen of catheter 29. The catheter 29 ends short of the control side end of the delivery device 25 and the filter 22 and the delivery device 25 sit inside the sheath lumen 62. For purposes of drawing clarity, the connection wiring to the ultrasound transducer is not illustrated. Delivery device 25 initially captures the four (4) longer struts 69 as part of the initial deployment and positioning of IVC filter 22.

Delivery apparatus 20 is introduced into the IVC 23 by way of wire guide 21 which extends through guide wire cannula 26. Wire guide 21 may remain in position during the delivery procedure described herein or may be removed once the delivery apparatus 20 is properly positioned as illustrated in FIG. 1. Wire guide 21 is important in the initial introduction of delivery apparatus 20, but the wire guide 21 is not necessary for proper removal of delivery apparatus 20. The advancing and positioning of wire guide 21 is performed using one of the existing technologies or methodologies. Some of the suitable choices for wire guide 21 include a fixed-core wire providing enhanced support, a "nitinol" wire providing shape memory and maneuverability and a hydrophilic wire with a lubricious coating for a low coefficient of friction.

The IVC filter 22 is constructed and arranged for use in capturing emboli, for example, a detached blood clot or a larger piece of a blood clot which is travelling in the blood stream through the IVC. One example of a suitable IVC filter for this application is a CELECT® Vena Cava Filter offered by Cook Medical of Bloomington, Ind. The outer sheath 24, also referred to as an introducer sheath, is constructed and arranged with a tubular wall 60 defining a lumen 62 formed therethrough. Preferably, for the use disclosed herein, the overall length of the delivery set, i.e. delivery apparatus 20, is approximately 65 cm. The gauge, using the "Fr" scale is approximately 8.5 Fr, or approximately 2.83 mm in outside diameter. The guide wire cannula 26 is constructed and arranged with a generally annular, tubular form with a generally circular shape in lateral section. The relationship between the guide wire cannula 26, the wire guide 21 and the catheter 29, including their respective sizes, shapes and materials, provides the desired support and stiffness and reduces any loads on the IVC filter 22 to suitable and acceptable levels.

The ultrasound transducer 28 is constructed and arranged for use in visualizing the deployment and positioning of the IVC filter 22 within the IVC 23. Considering the intravascular positioning and use of ultrasound transducer 28, the acronym, IVUS, is applicable and is used herein as a shorthand modifier for ultrasound transducer 28, i.e. IVUS transducer 28. This acronym is also used to reference and describe the manner of guiding the deployment and positioning of IVC filter 22. The dilator 30 is constructed and arranged with a tapered end 32 as the leading portion of delivery apparatus 20 entering the vein. The focus herein is on using the femoral vein approach for introduction of delivery apparatus 20 and emplacement of IVC filter 22.

In the exemplary embodiment, IVUS transducer 28 includes a stainless steel tubular core surrounded by a ceramic sleeve. Wrapped around the ceramic sleeve is a flexible printed circuit board. The IVUS transducer "mechanics" include an array constructed from a plurality of elements. The number of wires required for a multi-element phased array would be size prohibitive. Scanning options include a motor driven rotary transducer or alternatively a motor driven mirror with a fixed transducer. Due to size considerations, the motor would be external to the patient and would connect to either the rotary element of the transducer or to the mirror, by means of a rotary cable. Alternatively the motor could be micro-sized and incorporated into the application side end of the catheter.

Since apparatus 20 is an intravascular apparatus its size, shape and material selections are all consistent with apparata and devices which need to fit and move within a vein, for example. One of the important considerations in the manner or method of use of delivery apparatus 20 is the manner of guiding the IVC filter 22 into position. The "guiding" involves both the tracking of the delivery apparatus 20 and the deployment of the IVC filter 22 out of the delivery apparatus 20 for emplacement. The "guiding" also performs a check of the final placement and position of the IVC filter 22. One option for "guiding" an IVC filter is to use fluoroscopic guidance. However, using intravascular ultrasound (IVUS) for watching the positioning of the IVC filter 22 is considered to be an improvement over fluoroscopic guidance in terms of the required facilities and the mechanics of the steps to be performed. The design and construction of the delivery apparatus 20 takes the use of an IVUS transducer 28 to an improved level by integrating the IVUS transducer 28 directly into delivery apparatus 20.

Figure 2:
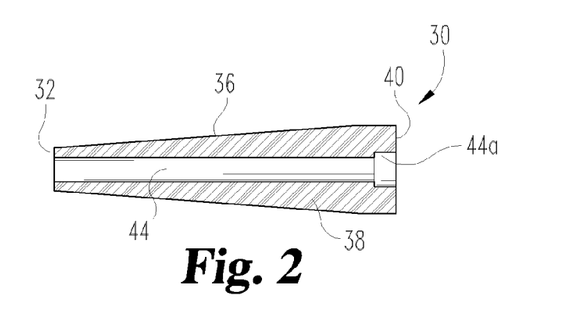
FIG. 2 is a side elevational view, in full section, of a dilator which comprises one of the components of the FIG. 1 delivery apparatus.
Figure 2A:
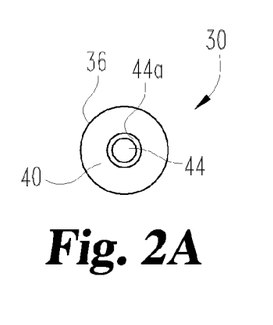
FIG. 2A is an end elevational view, in full form, of the FIG. 2 dilator.
Figure 3:
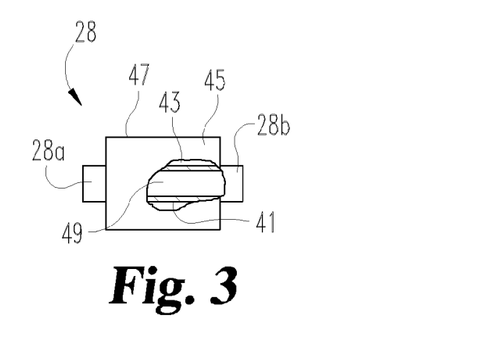
FIG. 3 is a fragmentary, side elevational view of an ultrasound transducer which comprises one of the components of the FIG. 1 delivery apparatus.
Figure 3A:
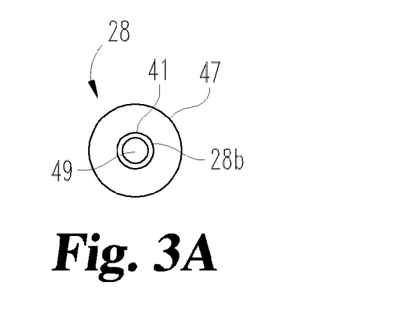
FIG. 3A is an end elevational view of the FIG. 3 ultrasound transducer.
Figure 4:
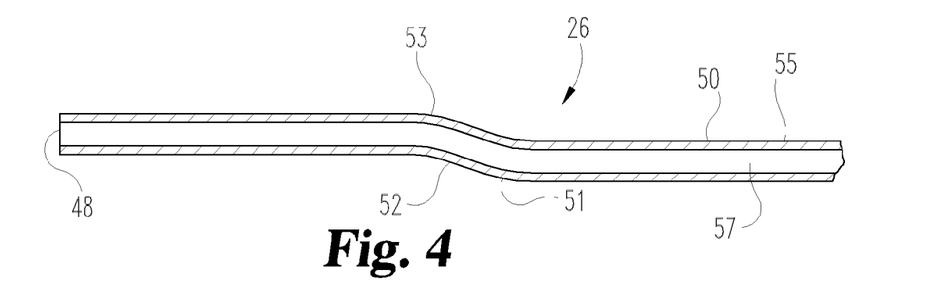
FIG. 4 is a side elevational view of a guide wire cannula which comprises one of the components of the FIG. 1 delivery apparatus.
Figure 4A:
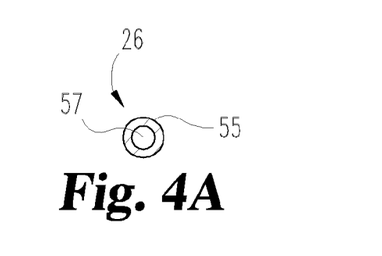
FIG. 4A is an end elevational view of the FIG. 4 guide wire cannula.
Figure 5:
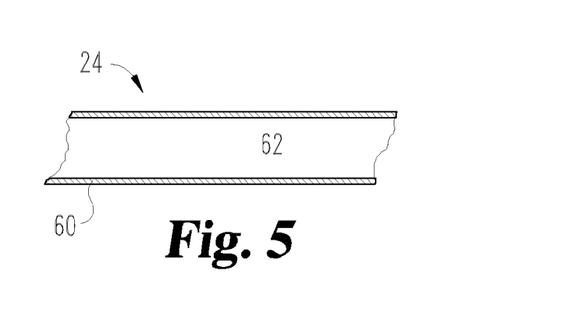
FIG. 5 is a side elevational view, in full section, of an outer sheath which comprises one of the components of the FIG. 1 delivery apparatus.
Figure 5A:
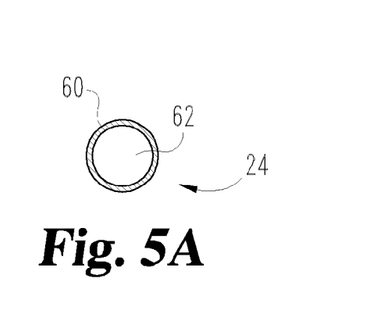
FIG. 5A is a end elevational view, in full form, of the FIG. 5 outer sheath.
Figure 6:
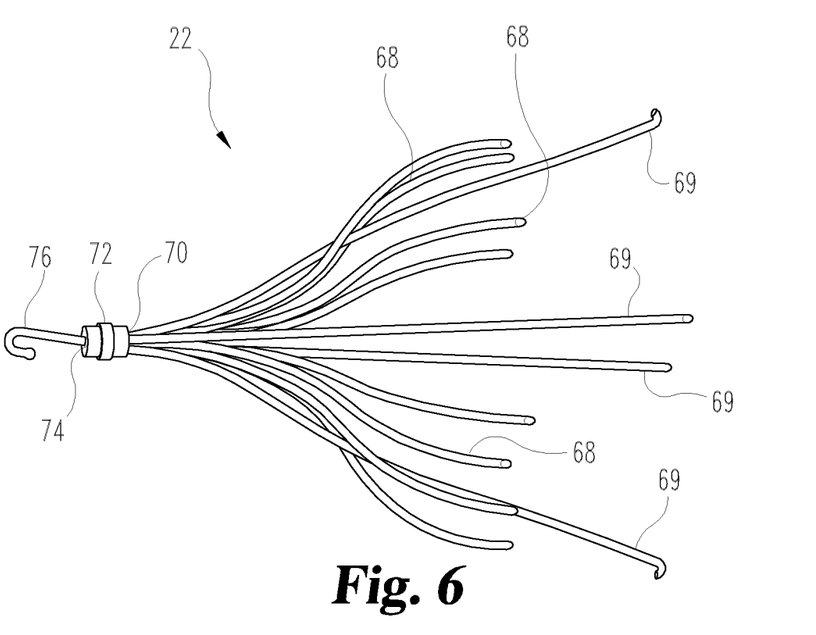
FIG. 6 is a diagrammatic, perspective view of an intravascular filter which comprises one of the starting components of the FIG. 1 delivery apparatus and which is delivered by the FIG. 1 delivery apparatus.

Referring to FIGS. 2-6, selected ones of the components which are part of delivery apparatus 20 are illustrated in greater detail. The details of dilator 30 are illustrated in FIGS. 2 and 2A. Some of the details of the IVUS transducer 28 are illustrated in FIGS. 3 and 3A. The details of guide wire cannula 26 are illustrated in FIGS. 4 and 4A. The details of outer sheath 24 are illustrated in FIGS. 5 and 5A. The details of IVC filter 22 are illustrated in FIG. 6.

Referring to FIGS. 2 and 2A, the dilator 30 includes a generally frustoconical body 36 with a tapering sidewall 38 converging from control side end 40 to application side end 32. Body 36 defines a coaxial central bore 44 which receives guide wire cannula 26. Counterbore 44a is coaxial with bore 44 and is sized and shaped to receive an application side hub portion of IVUS transducer 28. The guide wire cannula 26 in cooperation with wire guide 21 are used and assists in positioning the delivery apparatus 20 for IVC filter 22 deployment in the IVC 23. Removal of delivery apparatus 20 (without the IVC filter) after deployment does not require the continued use of wire guide 21. In order to properly perform these integrated functions, the application side end 48 of guide wire cannula 26 is securely anchored within central bore 44. The securement relationship preferably includes compatible sizes and shapes for the central bore 44 and the application side end 48. Dilator 30 is located at the application side end of the delivery apparatus 20 and receives the application side end of the guide wire cannula 26.

Referring to FIGS. 3 and 3A, IVUS transducer 28 has a generally cylindrical shape defined by body 45 and its generally cylindrical outer wall 47. Included for alignment and positioning is a first coaxial hub 28a and a second coaxial hub 28b. Hub 28a fits within counterbore 44a. The stainless steel core 41 which extends through body 45 has a generally cylindrical, tubular shape and defines central bore 49. Core 41 provides coaxial hubs 28a and 28b. Surrounding tubular core 41 is a generally cylindrical ceramic sleeve 43. A flexible printed circuit board (not illustrated) is wrapped around ceramic sleeve 43. The components of the printed circuit board face inwardly so as to provide added protection. The central bore 49 is constructed and arranged to receive a portion of guide wire cannula 26 therethrough. The control side end portion of IVUS transducer 28 is initially (see FIG. 1) received within the application side of lumen 62.

Figure 11:
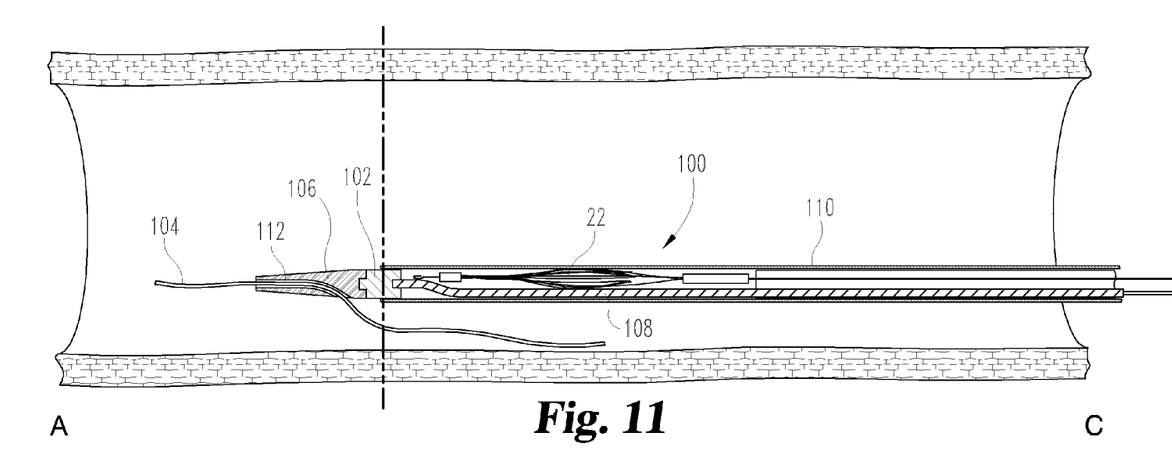
FIG. 11 is a partial, diagrammatic, side elevational view of an alternative transducer tip and wire guide arrangement according to the present disclosure.
Figure 12:
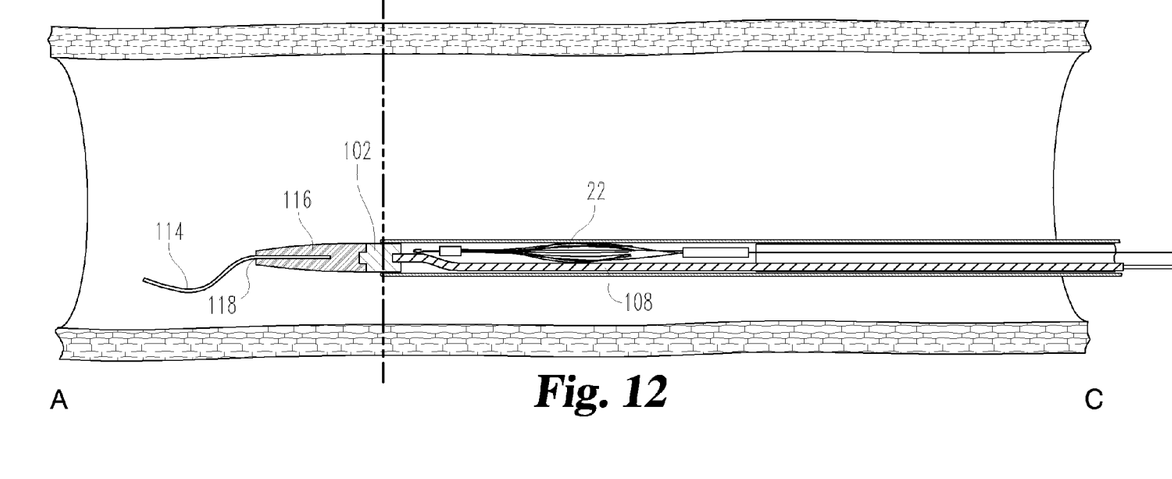
FIG. 12 is a partial, diagrammatic, side elevational view of an alternative transducer tip and wire guide arrangement according to the present disclosure.
Figure 13:
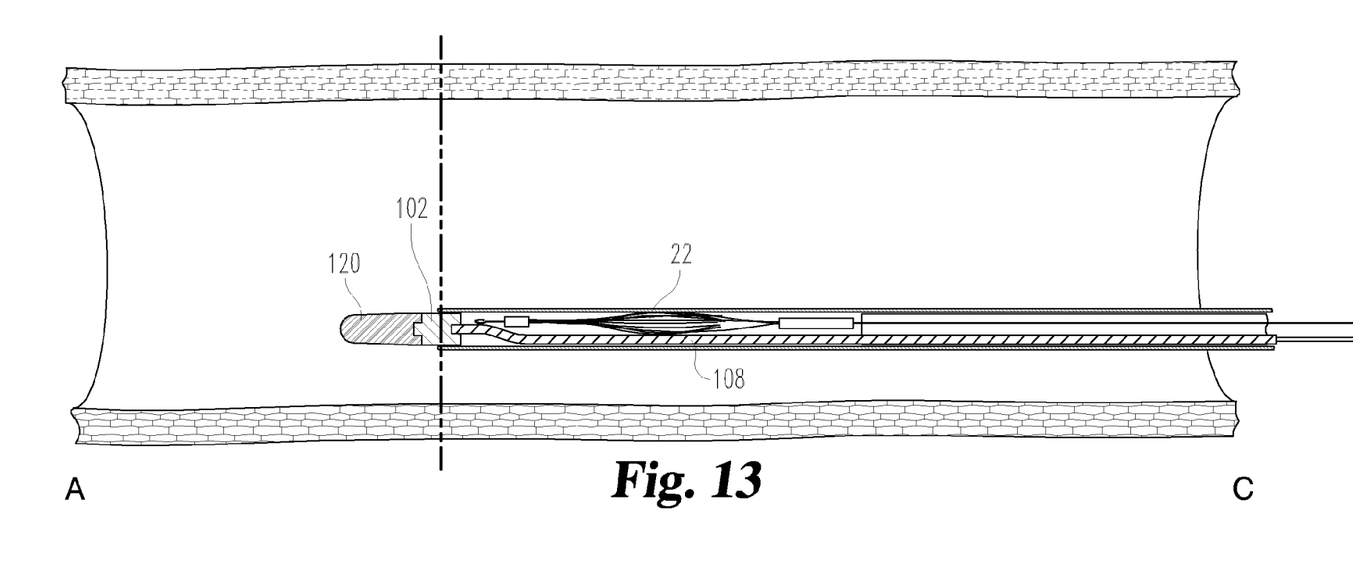
FIG. 13 is a partial, diagrammatic, side elevational view of an alternative transducer tip arrangement according to the present disclosure.

The construction represented by the exemplary embodiment of FIGS. 1-3A provides a specific arrangement and relationship between the guide wire cannula 26, guide wire 21, IVUS transducer 28 and dilator 30 (i.e. the tip of delivery apparatus 20). Alternative embodiments are illustrated in FIGS. 11-13 and each of these is described in greater detail hereinafter. Additionally, it is to be noted that the IVUS transducer selection, style, configuration and operation can be varied from what is disclosed for the exemplary embodiment. While one (1) variation is disclosed in FIGS. 11-13, it is further contemplated that a 3D scan capability can be integrated into the selected IVUS transducer. A 3D scan capability could include a single element transducer which is constructed and arranged to be motor driven into two (2) different mechanical axes. Another option for providing this 3D scan capability is to use a linear array transducer and drive it with rotary motion. Another option for providing this 3D scan capability is to use a full 2D linear array. For this option a row-column addressing scheme is used to access different elements for different transmit events.

Referring to FIGS. 4 and 4A, the guide wire cannula 26 has an annular, tubular shape with a sidewall 55 defining a hollow interior 57. The size of hollow interior 57 accommodates receipt of a wire guide in the size range of 0.035-0.040 inches. Although guide wire cannula 26 is described as having a generally tubular shape, guide wire cannula 26 would preferably have a generally cylindrical shape with a substantially uniform sidewall thickness. As such, the overall cannula 26 would have a generally circular shape in lateral section and the hollow interior 57 would preferably have a generally circular shape in lateral section, see FIG. 4A. The guide wire cannula 26 includes an application side end or tip 48, a control side portion 50 and two spaced-apart bends 51 and 53 which define ramp portion 52 therebetween. The tip 48 is located in the dilator 30 and extends through or passed the IVUS transducer 28. Portion 50 represents a section which extends through one of the lumen of catheter 29. The two bends 51, 53 create offset ramp portion 52. Ramp portion 52 is positioned adjacent hub 72 of the IVC filter 22 in the initial positioning illustrated in FIG. 1. This offset ramp portion 52 creates a shift in alignment from an edge position to a centered position which is essentially on-axis.

Referring to FIGS. 5 and 5A, the outer sheath 24 is an annular, flexible sleeve with an outer tubular wall 60 defining the hollow interior or lumen 62. Considering the function and use of outer sheath 24, suitable materials include polyethylene and other semi-flexible plastics. These materials represent durable, yet flexible, biocompatible materials which can be readily formed or extruded into the desired starting shape of a generally cylindrical tube or sleeve. The thickness of outer wall 60 depends in part on the selected material, but is generally in the range of 0.015-0.020 inches. Logically, a less durable or less tough material would require a slightly thicker wall. Since outer sheath 24 represents the radially outermost component, its interior size is selected so as to house the other components, except for dilator 30 and except for the application side end 48 of the guide wire cannula 26. At the same time, the maximum size of the outer tubular wall 60 must be limited and controlled for placement and travel within the IVC 23. Outer sheath 24 may have a length sufficient to extend outside the patient through a percutaneous entry to the emplacement location for the IVC filter 22. In such embodiments, for instance, a control side portion or end of outer sheath 24, and/or an operating portion attached to it, is outside the body, while an application side portion is adjacent the IVC filter 22 and initially extends over the end of IVUS transducer 28. Preferably, outer sheath 24 is of a semi-flexible plastic or other material, such as materials used for intravascular catheters, to allow it to move through vessels while maintaining integrity and allowing loading of the filter. Currently-available sheaths are sized to be small in diameter while still permitting a collapsed filter to fit within them, as is naturally suggested by placement of such sheaths in the vasculature.

Referring to FIG. 6, the IVC filter 22 includes a plurality of spring-biased wire legs or struts 68 and 69 which are constructed and arranged to include a plurality of shorter struts 68 and a plurality of longer struts 69. The shorter struts 68 are referred to as "secondaries". The longer struts 69 are referred to as "primaries". Struts 68 and 69 are securely anchored together by crimping into the control side end 70 of hub 72. The application side end 74 of hub 72 includes an outwardly-extending removal hook 76. Removal hook 76 extends in an application side direction beyond an application side end 74 of hub 72. Since removal hook 76 will be used in a subsequent procedure for the retrieval and removal of the IVC filter 22, it is important as part of the positioning and placement for IVC filter 22 (i.e. the emplacement) to have removal hook 76 properly positioned and oriented. It is also important for the removal hook 76 and the struts 68 and 69 to be securely connected together, whether by being crimped together into hub 72 or by some other method or structure. At the time of retrieval and removal of IVC filter 22, hook 76 will be used for the initial engagement by a loop of the retrieval apparatus. Pulling on the hook as part of the removal procedure will exert forces on the hub and in turn will exert forces on the struts tending to want to try and separate either the hook from the hub or the hub from the struts. Staying integrally connected and securely joined is important as part of the retrieval and removal procedure.

Referring now to FIGS. 7-10, and with continued reference to FIG. 1, these figures depict the structural configurations associated with the steps or stages in the delivery, deployment and positioning of the IVC filter 22 within the IVC 23, as well as the ultrasound imaging verification of that final positioning. These phases of delivery, deployment and positioning are collectively referred to herein as "emplacement". The starting stage or step in the method of delivery is represented by FIG. 1. This figure shows the delivery apparatus 20 as initially configured and as initially moved into position within the patient. The walls of the IVC 23 are represented by the two pairs of broken lines. The IVUS transducer 28 is constructed and arranged such that when energized in the intended manner, an imaging plane 84 is generated. It is important for the IVC filter 22 to be delivered to a location relative to the imaging plane. This allows the physician to precisely control the delivery location of the filter per his or her expertise. For the initial positioning of delivery apparatus 20 within the IVC, according to the exemplary embodiment, the imaging plane is at the lower renal vein of the patient and is represented by broken line 84 in FIG. 1. As would be understood, the drawing figures are diagrammatic and are not necessarily drawn to scale. The imaging plane 84 encompasses a radius of approximately 5 cm. This radius gives good coverage of the vena-cava wall and surrounding tissue.

Figure 7:
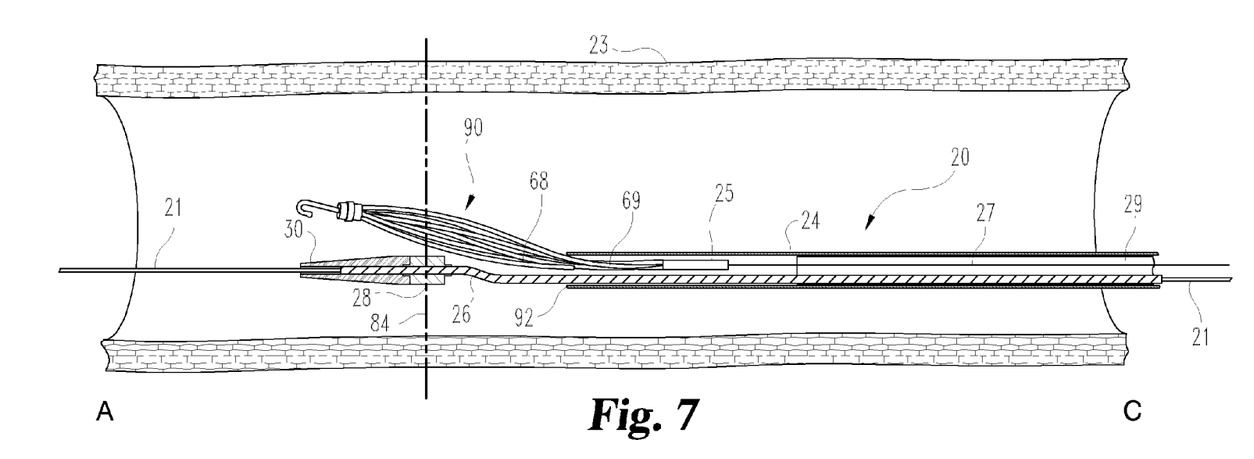
FIG. 7 is a diagrammatic illustration of one of the emplacement steps associated with the use of the FIG. 1 delivery apparatus.

Another step or stage in the method of delivery, as illustrated in FIG. 7, includes the step of pulling the outer sheath 24 back slightly in the control side direction. As the outer sheath 24 is pulled back, an opening 90 is created between the application side end 92 of the sheath 24 and the IVUS transducer 28. Another action, still referring to FIG. 7, is to advance the IVC filter 22. The IVC filter 22 is initially advanced in combination and cooperation with filter delivery device 25 and control wire 27. Once initially deployed, the next step is for the IVC filter 22 to be advanced out of the delivery apparatus which means out of outer sheath 24. As the outer sheath 24 is retracted the struts 68 are allowed to expand and the IVC filter 22 becomes generally centered in the IVC.

Figure 8:
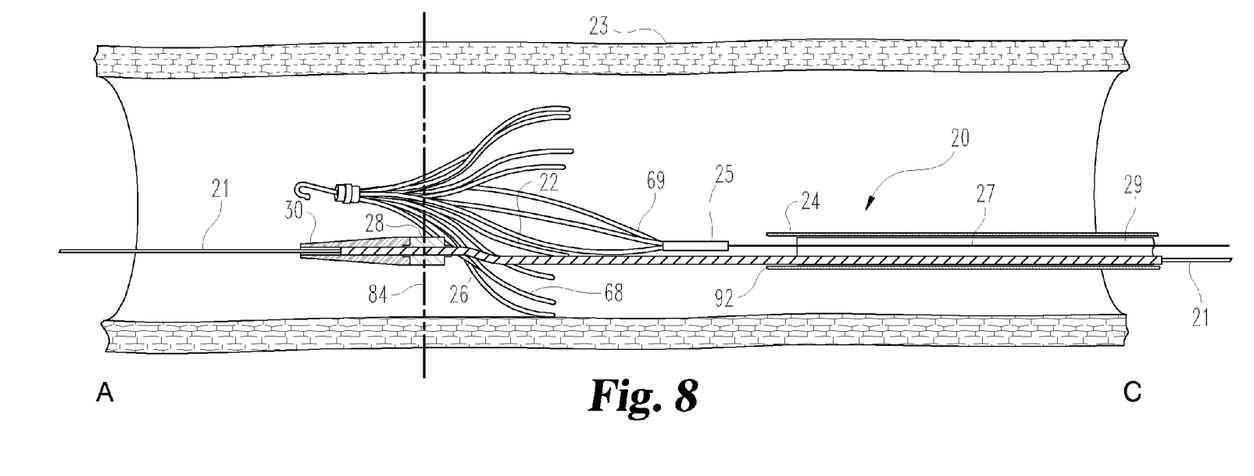
FIG. 8 is a diagrammatic illustration of another one of the emplacement steps associated with the use of the FIG. 1 delivery apparatus.

In conjunction with the deployment and positioning of IVC filter 22 as illustrated in FIGS. 7 and 8, it may be desired to rotate the delivery apparatus 20 in order to have a preferred orientation for the IVC filter 22 as it is deployed. Any such desired rotation needs to occur before the struts 68 are deployed. During these steps the filter delivery device 25 receives and secures the four (4) longer struts 69 which are effectively wedged together into a smaller bore section on the interior of device 25. The control wire pushes on the control side end of device 25 and in turn the wedged struts 69 get pushed by device 25, thereby pushing the entirety of the IVC filter 22. As the application side portion of IVC filter 22 is advanced, it finds its way to opening 90. The directing of the IVC filter 22 to and out through opening 90 can be improved upon by the shaping or contouring of the control side end of the IVUS transducer 28 in order to lessen the chances of any direct abutment and to improve the chances of providing a deflecting surface.

The guidance provided by the IVUS transducer 28 is used to stop the advancing of the IVC filter 22 once the removal hook 76 is in the imaging plane 84. As would be understood from what has been described, the outer sheath 24 is movable in a control side direction independently of the IVUS transducer 28. Similarly, the IVC filter 22 is movable in an application side direction independently of the IVUS transducer 28.

Figure 9:
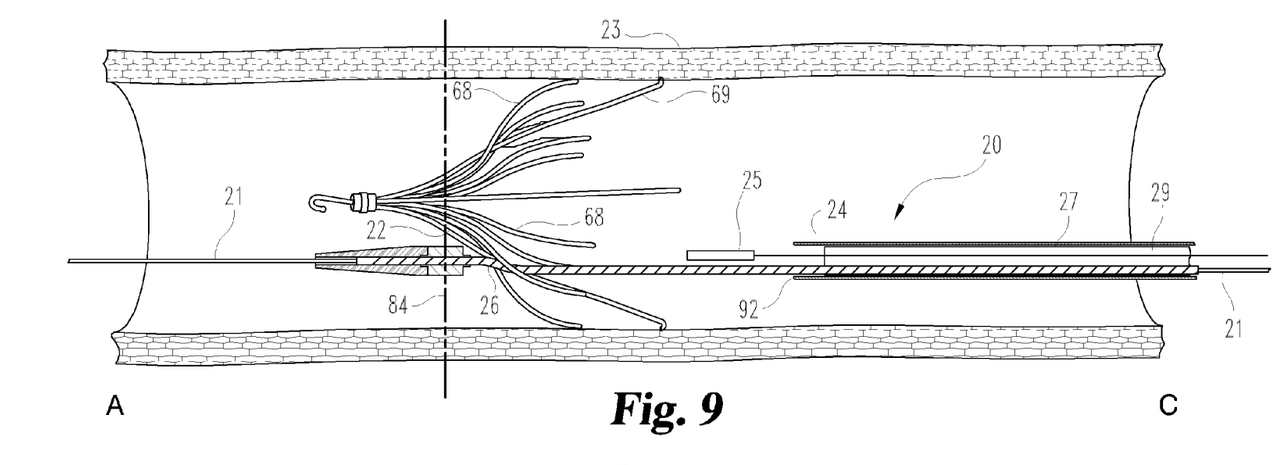
FIG. 9 is a diagrammatic illustration of another one of the emplacement steps associated with the use of the FIG. 1 delivery apparatus.
Figure 10:
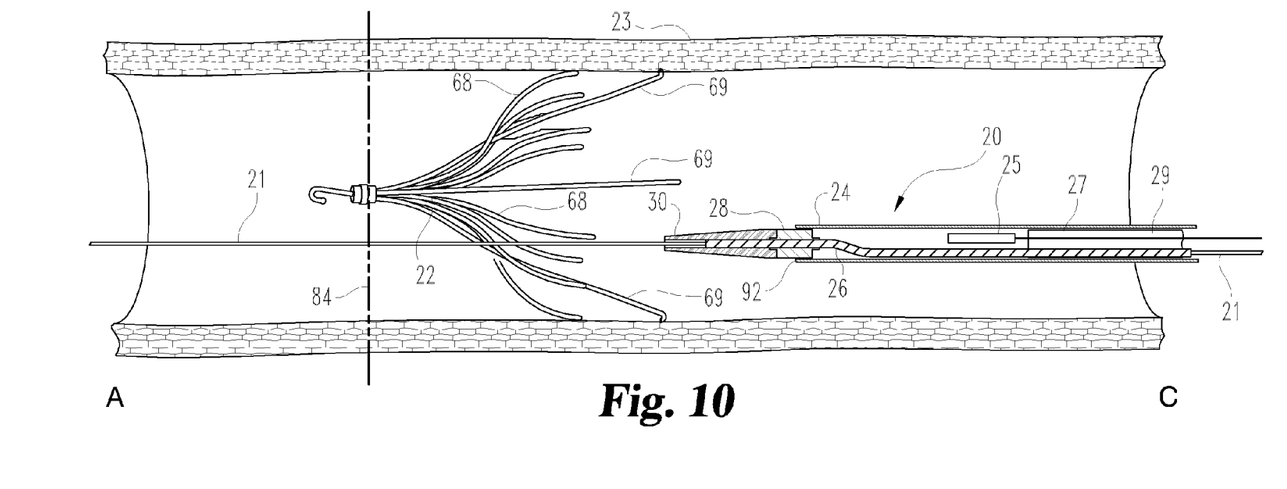
FIG. 10 is a diagrammatic illustration of another one of the emplacement steps associated with the use of the FIG. 1 delivery apparatus.

After rotation of the outer sheath 24 and catheter 29, so as to have a generally centered position for IVC filter 22 and for the desired orientation of hook 76, the next step is to pull back the outer sheath 24 in the control side direction and allow the secondary struts 68 of the IVC filter 22 to expand. With the secondary struts 68 fully deployed (see FIG. 9) across the interior of IVC 23, the remainder of delivery apparatus 20 is withdrawn and removed (see FIG. 10). The initial stage of withdrawing creates movement of the filter delivery device 25 in a control side direction. In the exemplary embodiment the longer struts 69 are deployed via a release mechanism connected to device 25. Retracting the catheter alone is not sufficient and device 25 is configured specifically to prevent inadvertent premature deployment. The struts 69 now move from their wedged retention in device 25 to a wider opening of device 25 and ultimately out of device 25. The longer struts 69, having a greater length, extend outwardly into contact with the wall of the IVC 23. The initial release of the struts 69 from device 25 is illustrated in FIG. 9. The full release and expansion of struts 68 and 69 is illustrated in FIG. 10.

The use herein of "remainder" in the context of the delivery apparatus 20 refers to the fact that while the IVC filter 22 is initially included as a part of delivery apparatus 20, once the IVC filter 22 is deployed in the vein (i.e. emplaced), the "remainder" of delivery apparatus 20 is without the IVC filter 22. An IVUS pullback data set is recorded as the remainder of the delivery apparatus is withdrawn and removed. The recorded data set serves as a medical record verifying correct placement of the IVC filter 22. As would be understood from what has been described, the outer sheath 24 and the IVC filter 22 are each cooperatively constructed and arranged such that rotation of the outer sheath 24 causes rotation of the IVC filter 22.

A further feature which may be included as part of delivery apparatus 20 is the addition of a ruler printed on the outer surface of sheath 24. The addition of a printed ruler to the sheath 24 improves contextual awareness during the procedure which can be difficult during IVUS guided procedures. The depth information (via visualization of the ruler) can also be used to plan and verify placement.

A still further feature which may be included as part of delivery apparatus 20 is to modify the construction of IVC filter 22 with the addition or inclusion of echogenic features in order to improve the visibility of the IVC filter 22 when imaged by ultrasound.

Recognizing that an exemplary embodiment of the disclosed delivery apparatus has been described herein, it may be helpful for a complete understanding of the possible variations and options, to consider the following. First, the delivery procedure which includes a step of rotation so that the filter hook 76 is angularly aligned to be near the center of the IVC is optional. This centering is not currently done under fluoroscopic guidance and is optional under IVUS guidance. When the struts 68 expand, the hook 76 is naturally pushed toward the center of the IVC. The IVC filter 22 is therefore self-centering in most instances. The angular alignment step, when performed, is expected to further reduce the already small chance of an un-centered deployment.

Further, the angular alignment step does not necessarily require that the hook be advanced into the IVUS imaging plane as in FIG. 7. The same functionality can be achieved by aligning the IVUS transducer and filter during manufacturing and configuring the console to indicate the orientation of the filter relative to the IVUS image. This configuration eliminates the need to have the IVUS transducer 28 and the filter holder 25 configured so that they can move independently.

As a further design variation, it is possible to include a rotational transducer assembly. In this type of design the transducer is not hollow and therefore the guide wire lumen cannot be run through the center of the transducer. If a traditional torque cable is used to drive the rotation, guide wire cannula 26 would be used to house the torque cable. If an on-site motor is used, then the guide wire cannula 26 does not need to be hollow and would provide mechanical support only. In order to accommodate a rotating transducer, an alternative guide wire routing is required. The guide wire could be permanently glued into the dilator lumen 44 with a fixed length protruding from the application side end of the dilator tip. Alternatively, lumen 44 could exit the dilator lumen on the control side portion of the side of the dilator 36 forming a rapid exchange type wire guide system.

By incorporating the IVUS transducer 28 into delivery apparatus 20, the entire ultrasound procedure is able to be performed without removing the IVUS transducer 28. This design aspect means that during dilation, sheath placement, filter delivery and IVC filter placement verification, the clinician can feel safe because the clinician is able to "see", in terms of ultrasound imaging, what is happening. The disclosed method or procedure does not have any steps which require the clinician "going blind" which would be a potential safety concern. Further, since the IVUS transducer 28 stays in the patient, no catheter exchanges are required. This significantly speeds up and simplifies the procedure. By positioning the IVUS transducer 28 in front (i.e. to the application side) of the IVC filter 22, IVC filter placement can be performed without having to push the catheter through the IVC filter 22. Otherwise, this would be a potential safety risk because it is possible to get the catheter caught in the IVC filter apex and move the IVC filter accidently. By means of the disclosed embodiment of delivery apparatus 20, the IVC filter 22 is able to be delivered safely, quickly and easily under ultrasound guidance. This approach, as embodied by the present disclosure, is considered to be an improvement to the prior art approach using fluoroscope guided delivery sets. The delivery apparatus 20 is able to be introduced and removed through a single access site.

Referring now to FIGS. 11-13, three (3) other embodiments for the application side end of a delivery apparatus are illustrated. Referring first to FIG. 11, an IVUS filter delivery apparatus 100 is disclosed which includes an embedded IVUS transducer 102. This embodiment offers design options for the IVUS transducer 102, the "rapid exchange" wire guide 104 and the tip 106. This embodiment is not dependent on the specific configuration of the IVUS transducer 102.

Optionally, the IVUS transducer may be hollow or may not be hollow, the latter being disclosed as IVUS transducer 102. As such, the alternatives which are available and compatible with the illustrated structure of delivery apparatus 100 include, as one (1) option, the use of a torque cable driven transducer. Other options include the use of an on-site motor rotary transducer, array transducers and 3D transducers in a variety of configurations.

The delivery apparatus includes an IVUS filter 22 and a mechanical support 108 which provides a connection between the application side or end of the catheter 110 where the tip 106 and transducer 102 are positioned and the control side or end where the IVUS filter 22 and the main body of the catheter 110 are positioned.

In the exemplary embodiment of FIG. 11, the mechanical support 108 is hollow and is constructed and arranged to be able to receive a wire guide, transducer cabling, a torque cable, a fluid lumen, etc. Alternatively, the mechanical support may be a solid member. The application side or end, denoted by the letter A, includes the tip 106 which is adjacent one (1) end of the transducer 102.

As illustrated in FIGS. 11, 12 and 13, several design options are available for the transducer tip 106. One (1) option associated with the FIG. 11, is to configure the transducer tip 106 with a rapid-exchange lumen 112. Another option, associated with FIG. 12, is to configure the wire guide 114 and transducer tip 116 such that one (1) end of the wire guide 114 is permanently embedded into a receiving aperture 118 in the application side or end of the transducer tip 116. Another option, associated with FIG. 13, is to eliminate the wire guide (104, 114) and instead round or contour the application side or end of tip 120 with a substantially hemispherical shape. This substantially hemispherical shape at the leading edge or face reduces the risk of puncture or tearing of a vessel as the corresponding delivery apparatus is moved into the desired position.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A delivery apparatus for introducing an intravascular filter into a body vessel of a patient, said delivery apparatus comprising:
    a sheath having an annular wall defining a lumen;
    an intravascular filter positioned in said lumen, said intravascular filter having primary struts and secondary struts cooperatively arranged for a two-step deployment into said body vessel, said secondary struts being constructed and arranged for deployment first and said primary struts being constructed and arranged for deployment second;
    a delivery device positioned in said lumen, each primary strut having an end secured to a common hub and an opposite free end which is captured within said delivery device for said two-step deployment of said intravascular filter and each secondary strut having an end secured to said common hub and an opposite free end; and
    an ultrasound transducer positioned to an application side of said intravascular filter, wherein introduction of said intravascular filter into said body vessel includes release of said free ends of the primary struts from within said delivery device as the second step of said two-step deployment.

2. The delivery apparatus of claim 1 which includes a guide wire cannula extending through said lumen and including an application side end.

3. The delivery apparatus of claim 1 which includes a dilator located at an application side end of said delivery apparatus.

4. The delivery apparatus of claim 1 wherein said ultrasound transducer is constructed and arranged for providing a 3D scan capability.

5. The delivery apparatus of claim 1 which further includes a control wire which is cooperatively arranged with said delivery device.

6. The delivery apparatus of claim 1 which further includes means for releasing said primary struts from said delivery device, said means for releasing being independent of said sheath.

7. A delivery apparatus for introducing an intravascular filter into a body vessel of a patient, said delivery apparatus comprising:
    a sheath having an annular wall defining a lumen;
    an intravascular filter positioned in said lumen, said intravascular filter having primary struts and secondary struts cooperatively arranged for a two-step deployment into said body vessel, said secondary struts being constructed and arranged for deployment first and said primary struts being constructed and arranged for deployment second;
    a delivery device positioned in said lumen, each primary strut having an end secured to a common hub and an opposite free end which is captured within said delivery device for said two-step deployment of said intravascular filter and each secondary strut having an end secured to said common hub and an opposite free end, said secondary struts being free of retention within said delivery device;
    an ultrasound transducer positioned to an application side of said intravascular filter, wherein introduction of said intravascular filter into said body vessel includes release of said free ends of the primary struts from within said delivery device as the second step of said two-step deployment;
    a guide wire cannula extending through said lumen and including an application side end; and
    a dilator located at an application side end of said delivery apparatus, said dilator receiving the application side end of said guide wire cannula.

8. The delivery apparatus of claim 7 wherein said primary struts have a wedged retention within said delivery device.

9. The delivery apparatus of claim 7 wherein said intravascular filter further includes a removal hook.

10. The delivery apparatus of claim 9 wherein said removal hook is constructed and arranged to extend beyond an application side face of said hub.

11. The delivery apparatus of claim 9 wherein said hub is adjacent a ramp portion of said guide wire cannula.

12. The delivery apparatus of claim 7 wherein a control side portion of said ultrasound transducer is received within the lumen of said sheath.

13. The delivery apparatus of claim 7 wherein said guide wire cannula includes an application side portion, a control side portion and a ramp portion which is located between said application side portion and said control side portion.

14. The delivery apparatus of claim 7 wherein said sheath is constructed and arranged to be movable in a control side direction independently of said ultrasound transducer.

15. The delivery apparatus of claim 7 wherein said intravascular filter is constructed and arranged to be movable in an application side direction independently of said ultrasound transducer.

16. The delivery apparatus of claim 7 wherein said sheath and said intravascular filter are each cooperatively constructed and arranged such that rotation of said sheath causes rotation of said intravascular filter.

17. The delivery of claim 7 wherein said intravascular filter comprises an echogenic feature, thereby improving visibility of said intravascular filter when imaged by ultrasound.

18. The delivery apparatus of claim 7 which further includes a control wire which is cooperatively arranged with said delivery device.

19. The delivery apparatus of claim 7 wherein said secondary struts are captured by said sheath, wherein said delivery device and said primary struts captured within are together capable of being moved independently of said sheath.

20. A delivery apparatus for placing an inferior vena cava (IVC) filter in an IVC of a patient, said delivery apparatus comprising:
   a sheath having an annular wall defining a lumen;
   an IVC filter positioned in said lumen, said IVC filter having primary struts and secondary struts cooperatively arranged for a two-step deployment into said IVC, said secondary struts being constructed and arranged for deployment first and said primary struts being constructed and arranged for deployment second;
   a delivery device positioned in said lumen, each primary strut having an end secured to a common hub and an opposite free end which is captured within said delivery device for said two-step deployment of said IVC filter and each secondary strut having an end secured to said common hub and an opposite free end, said delivery device having an application side end;
   an intravascular ultrasound (IVUS) transducer positioned on an application side of said IVC filter, wherein introduction of said IVC filter into said IVC includes release of said free ends of the primary struts from within said delivery device as the second step of said IVC filter two-step deployment, and wherein a plurality of said primary and secondary struts of said IVC filter are positioned between said application side end of said delivery device and said IVUS transducer;
   a guide wire cannula extending through said lumen and terminating on an application side of said IVUS transducer; and
   a dilator assembled to said guide wire cannula, said IVUS transducer being positioned between said dilator and said IVC filter.

21. The delivery apparatus of claim 20 wherein said IVC filter includes a removal hook.

22. The delivery apparatus of claim 20 wherein said guide wire cannula includes an application side portion, a control side portion and a ramp portion which is located between said application side portion and said control side portion.

23. The delivery apparatus of claim 20 wherein said IVC filter is constructed and arranged to be movable independently of said IVUS transducer.

24. The delivery apparatus of claim 20 wherein said sheath and said IVC filter are each cooperatively constructed and arranged such that rotation of said sheath causes rotation of said IVC filter.

25. The delivery apparatus of claim 20 which further includes a control wire which is cooperatively arranged with said delivery device.

26. A method of introducing an intravascular filter into a body vessel of a patient using a delivery apparatus which includes a sheath, an intravascular filter including primary struts and secondary struts, a delivery device for deployment of said intravascular filter, an ultrasound transducer, a guide wire cannula and a dilator, each primary strut having an end secured to a common hub and an opposite free end captured within said delivery device, each secondary strut having an end secured to said common hub and an opposite free end, wherein said ultrasound transducer having an imaging plane, said method comprising the following steps:
   providing said delivery apparatus;
   inserting said delivery apparatus into the body vessel of the patient;
   positioning said delivery apparatus such that said imaging plane coincides with a selected location within the patient;
   deploying said intravascular filter in two stages with the secondary struts being deployed first followed by the primary struts being deployed by said free ends of the primary struts being released from within said delivery device; and
   withdrawing said delivery apparatus less said intravascular filter which remains in said body vessel.

27. The method of claim 26 wherein said intravascular filter includes a removal hook, and wherein the method further includes a manipulating step which includes positioning said removal hook in said imaging plane.

28. The method of claim 26 further includes the step of rotating the sheath for orienting said intravascular filter in order to achieve a desired orientation for said intravascular filter.

29. The method of claim 26 which further includes the step of imaging the intravascular filter placement as the ultrasound transducer is withdrawn.

* * * * *